United States Patent
Aoyagi

(10) Patent No.: US 11,864,835 B2
(45) Date of Patent: Jan. 9, 2024

(54) PUNCTURE SUPPORT DEVICE FOR DETERMINING SAFE LINEAR PUNCTURE ROUTES BY PUNCTURE REGION CLASSIFICATION AND SUPERIMPOSING OF IMAGES

(71) Applicant: TOSHIBA MEDICAL SYSTEMS CORPORATION, Otawara (JP)

(72) Inventor: Kota Aoyagi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 853 days.

(21) Appl. No.: 16/034,678

(22) Filed: Jul. 13, 2018

(65) Prior Publication Data

US 2018/0325600 A1 Nov. 15, 2018

Related U.S. Application Data

(60) Division of application No. 14/308,168, filed on Jun. 18, 2014, now abandoned, which is a continuation of
(Continued)

(30) Foreign Application Priority Data

Nov. 9, 2012 (JP) ................. 2012-247702

(51) Int. Cl.
*A61B 34/10* (2016.01)
*A61B 5/00* (2006.01)
(Continued)

(52) U.S. Cl.
CPC .............. *A61B 34/10* (2016.02); *A61B 5/489* (2013.01); *A61B 6/12* (2013.01); *A61B 8/0841* (2013.01);
(Continued)

(58) Field of Classification Search
CPC ......... A61B 34/10; A61B 90/37; A61B 5/489; A61B 17/3403; A61B 6/12; A61B 8/0841;
(Continued)

(56) References Cited

U.S. PATENT DOCUMENTS 6,961,608 B2 11/2005 Hoshino et al.
7,920,911 B2 4/2011 Hoshino et al.
(Continued)

FOREIGN PATENT DOCUMENTS

JP 2005-169070 A 6/2005
JP 2007-130287 A 5/2007
(Continued)

OTHER PUBLICATIONS

Shamir et al.(A Method for Planning Safe Trajectories in Image-Guided Keyhole Neurosurgery, MICCAI 2010, Part III, LNCS 6363, pp. 457-464, 2010).*
(Continued)

*Primary Examiner* — Serkan Akar
(74) *Attorney, Agent, or Firm* — Oblon, McClelland, Maier & Neustadt, L.L.P.

(57) ABSTRACT

A puncture support device includes a display unit, a puncture target setting unit, a puncturable region setting unit, a puncture route extraction unit, a safety degree calculation unit, and an insertion point candidate region display control unit. The puncture target setting unit is configured to set a puncture target in a acquired volume data. The puncturable region setting unit is configured to set a puncturable region on a body surface image. The puncture route extraction unit is configured to extract a puncture route from the set puncturable region on the body surface image to the puncture target. The safety degree calculation unit is configured to calculate a safety degree of the extracted puncture route.

(Continued)

The insertion point candidate region display control unit is configured to divide the puncturable region into groups based on the calculated safety degree, and display the divided region on the display unit.

9 Claims, 15 Drawing Sheets

Related U.S. Application Data application No. PCT/JP2013/080283, filed on Nov. 8, 2013.

(51) Int. Cl.
*A61B 8/08* (2006.01)
*A61B 17/34* (2006.01)
*A61B 6/00* (2006.01)
*A61B 6/12* (2006.01)
*A61B 90/00* (2016.01)
*A61B 6/03* (2006.01)

(52) U.S. Cl.
CPC ........ *A61B 17/3403* (2013.01); *A61B 90/37* (2016.02); *A61B 6/032* (2013.01); *A61B 6/5211* (2013.01); *A61B 8/0833* (2013.01); *A61B 8/483* (2013.01); *A61B 8/5215* (2013.01); *A61B 2034/107* (2016.02); *A61B 2090/366* (2016.02)

(58) Field of Classification Search
CPC ........ A61B 2034/107; A61B 2090/366; A61B 6/032; A61B 6/5211; A61B 8/0833; A61B 8/483; A61B 8/5215
See application file for complete search history.

(56) References Cited

U.S. PATENT DOCUMENTS

| 8,102,392 B2 | 1/2012 | Yamagata et al. |
| 2002/0058868 A1 | 5/2002 | Hoshino |
| 2005/0033160 A1 | 2/2005 | Yamagata |
| 2009/0137907 A1 | 5/2009 | Takimoto et al. |

FOREIGN PATENT DOCUMENTS

| JP | 2009-125280 A | 6/2009 |
| JP | 2010-099193 A | 5/2010 |
| JP | 2012-066148 A | 4/2012 |

OTHER PUBLICATIONS

Bériault et al (A multi-modal approach to computer-assisted deep brain stimulation trajectory planning, Int J CARS (2012) 7:687-704).*
International Search Report dated Dec. 3, 2013 for PCT/JP2013/080283 field Nov. 8, 2013 with English Translation.
International Preliminary Report on Patentability and Written Opinion dated May 12, 2015 in PCT/JP2013/080283.
Seitel et al., Computer-assisted trajectory planning for percutaneous needle insertions, Medical Physics, vol. 38, No. 6, Jun. 2011.

* cited by examiner

PUNCTURE SUPPORT DEVICE FOR DETERMINING SAFE LINEAR PUNCTURE ROUTES BY PUNCTURE REGION CLASSIFICATION AND SUPERIMPOSING OF IMAGES

CROSS-REFERENCE TO RELATED APPLICATION

This application is a divisional application of U.S. application Ser. No. 14/308,168, filed Jun. 18, 2014, which is a Continuation Application of No. PCT/JP2013/080283, filed on Nov. 8, 2013, and the PCT application is based upon and claims the benefit of priority from Japanese Patent Application No. 2012-247702, filed on Nov. 9, 2012. The entire contents of the above-identified applications are incorporated herein by reference.

FIELD

Embodiments of the present invention relate to a puncture support device.

BACKGROUND

In recent years, treatment by puncture has been often performed. The puncture refers to externally inserting an injection needle (puncture needle) into the blood vessel, the inside of the body cavity, or the internal organ. The treatment by puncture is performed to draw out a body fluid or pus accumulated in the body of a patient, or inject a drug. The puncture is also used to collect tissue from the inside of the body of the patient. Widely performed treatment at present is such that an operator manually inserts a puncture needle into the body of a patient while observing a real-time image of the inside of the body of the patient taken using an ultrasonic diagnostic device.

A detailed treatment method using puncture (puncture treatment for hepatocellular cancer) will be described. Presently known treatment methods for non-progressive hepatocellular cancer include surgical hepatectomy and local treatment.

The surgical hepatectomy is generally applied to a patient with good liver function, and medical treatment is selected for a patient with bad liver function. In the hepatectomy, a resection volume and invasion on the liver depend on the size and site of the tumor. The liver has a high capability of regeneration, and with sufficient liver reserve that indicates the function of the liver itself, nearly 80% of the entire liver can be resected, and the liver returns to its original size in about one year due to the capability of regeneration of the liver. However, with bad liver function, the liver cannot regenerate after the hepatectomy, and may be exhausted to result in liver failure.

On the other hand, the local treatment mainly includes percutaneous ethanol injection therapy by puncturing hepatocellular cancer and injecting ethanol to destroy cancer tissue, and radiofrequency thermocoagulation by applying radiofrequency radiation to destroy cancer tissue.

A large amount of blood flows in the liver, and if the puncture damages a main blood vessel, normal liver tissue other than the hepatocellular cancer that the blood vessel nourishes may be damaged. Also, when the hepatocellular cancer is located on the liver surface, the radiofrequency thermocoagulation also transmits heat to the diaphragm or pleura in contact with the liver, which may cause heat damage or thereby complications. Thus, for the local treatment, planning and implementation of a safe puncture route is very significant.

An image processing display device is disclosed in which a sectional image of a target including a puncture target is rotationally displayed around the puncture target in a three-dimensional image including the puncture target in treatment by puncture. In this image processing display device, an operator can check whether a puncture route does not include a target to be protected such as a blood vessel while changing sectional images of a subject to be the target.

Conventional puncture planning has an object to specify a route to safely reach a predetermined puncture target. However, it cannot be said that there is only one route to safely reach the predetermined puncture target, but actually, there may be a plurality of candidate routes.

Also, in actual puncture, the operator specifies an insertion point of a puncture needle in a puncture route determined by the puncture planning on the body surface of the subject.

However, by the puncture planning, the puncture route is set on a sectional image, and it is difficult for the operator to find the insertion point of the puncture needle on the body surface.

Specifically, in the conventional puncture planning, only one puncture route can be specified although there are a plurality of puncture routes for safely puncturing a puncture target, and also the puncture route can be set only on the sectional image including the puncture target. Thus, it is difficult for the operator to find an optimum insertion point of the puncture needle.

DETAILED DESCRIPTION

A puncture support device according to this embodiment includes: a display unit; a volume data acquisition unit configured to acquire three-dimensional volume data; a puncture target setting unit configured to set a puncture target in the acquired volume data; a puncturable region setting unit configured to set a puncturable region on a body surface image extending from the body surface to the set puncture target in the acquired volume data; a puncture route extraction unit configured to extract a puncture route from the set puncturable region on the body surface image to the puncture target; a safety degree calculation unit configured to calculate a safety degree of the extracted puncture route; and a insertion point candidate region display control unit configured to divide the puncturable region into groups based on the calculated safety degree, set a candidate region of a puncture insertion point for puncturing the puncture target in a puncturable region belonging to a predetermined group, and display the candidate region on the display unit.

Thus, the puncture support device according to this embodiment can display candidate regions of a plurality of puncture routes for safely puncturing the puncture target, and display the candidate region of the puncture insertion point on the body surface image.

First Embodiment

Now, a workstation (puncture support device) 300 according to a first embodiment will be described with reference to the drawings.

Figure 1:
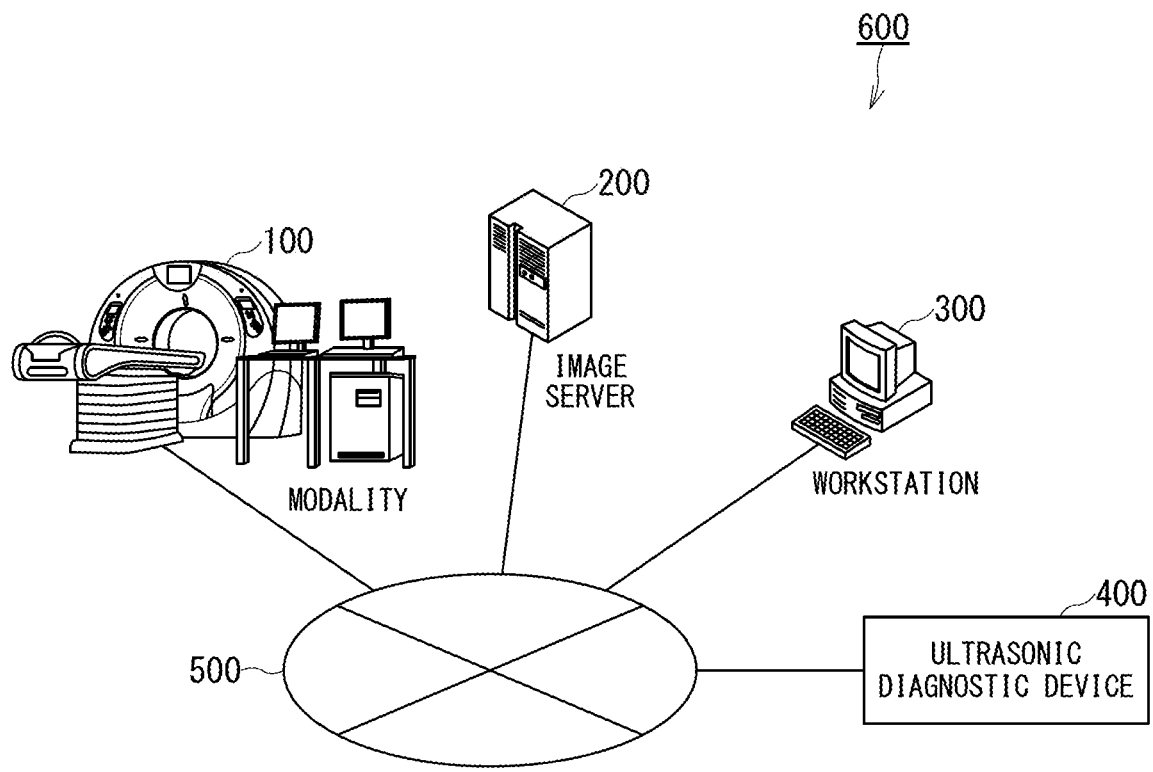
FIG. 1 is a schematic configuration diagram showing an example of a schematic configuration of a puncture system using a workstation according to the first embodiment.

FIG. 1 is a schematic configuration diagram showing an example of a schematic configuration of a puncture system 600 using the workstation 300 according to the first embodiment.

As shown in FIG. 1, the puncture system 600 includes a modality 100, an image server 200, a workstation 300, an ultrasonic diagnostic device 400, a network 500, or the like.

The modality 100 refers to a medical system used for classifying devices for imaging a subject (imaging devices). For example, the modality 100 includes an X-ray CT (Computed Tomography) device, an MRI (Magnetic Resonance Imaging) device, an ultrasonic diagnostic device, or the like. The X-ray CT device is a tomography device for scanning an object with radiation or the like and processing with a computer. The MRI device is a device for taking an image of the inside of the body of a subject using magnetic fields and radio waves. The ultrasonic diagnostic device is an image diagnostic device that applies ultrasonic waves to a subject and visualizes echoes thereof. In this embodiment, any of the devices may be applied as the modality 100 as long as they can image three-dimensional volume data.

The image server 200 is an image management server that constitutes a medical image management system (PACS: Picture Archiving and Communication System), and stores, browses, and manages three-dimensional volume data acquired by the modality 100 imaging a subject (patient).

The workstation (puncture support device) 300 is a device for performing computer processing of three-dimensional volume data acquired by the modality 100 imaging the subject or three-dimensional volume data stored in the image server 200 to visualize a three-dimensional display or perform a quantitative analysis. The workstation 300 according to this embodiment includes a medical image processing device. Details of the workstation 300 according to this embodiment will be described later.

The ultrasonic diagnostic device 400 images a position of an affected area of the subject or a puncture needle acquired by an ultrasonic probe in puncture, and displays the imaged site. In this embodiment, the ultrasonic diagnostic device 400 is adopted as a device for puncture for description, but an X-ray CT device or an MRI device may be used as long as they can be used for puncture.

The network 500 interconnects devices that are connected to the puncture system 600.

Next, the configuration of the workstation 300 according to the first embodiment will be described in detail.

Figure 2:
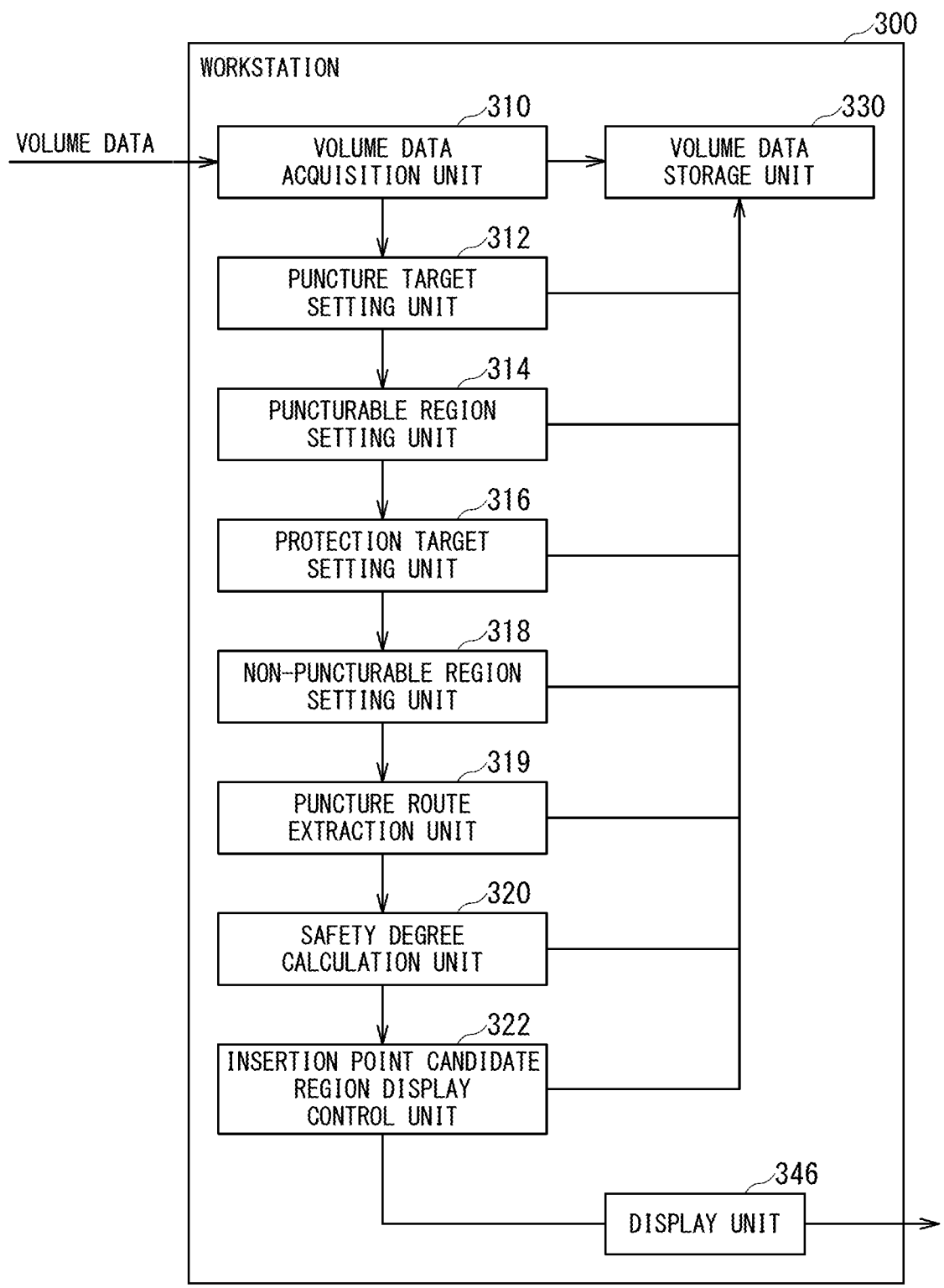
FIG. 2 is a functional block diagram showing a function of the workstation according to the first embodiment.

FIG. 2 is a functional block diagram showing a function of the workstation 300 according to the first embodiment.

As shown in FIG. 2, the workstation 300 includes a volume data acquisition unit 310, a puncture target setting unit 312, a puncturable region setting unit 314, a protection target setting unit 316, a non-puncturable region setting unit 318, a puncture route extraction unit 319, a safety degree calculation unit 320, an insertion point candidate region display control unit 322, a volume data storage unit 330, and a display unit 346, or the like.

The volume data acquisition unit 310 acquires three-dimensional volume data imaged by the modality 100 and stored in the image server 200 (FIG. 1). The volume data acquisition unit 310 stores the acquired volume data in the volume data storage unit 330.

The puncture target setting unit 312 sets a puncture target in the acquired volume data. When the puncture target setting unit 312 sets the puncture target in the volume data, the puncture target setting unit 312 stores the volume data with the set puncture target in the volume data storage unit 330.

The puncture target setting unit 312 sets a puncture target in such a manner that, as an example, a three-dimensional reconfiguration unit (not shown) reconfigures volume data as voxel data suitable for three-dimensional image processing, and then reconfigures the data as a volume rendering image. However, when a puncture target can be extracted from the volume data by software, the puncture target may be automatically set.

The puncturable region setting unit 314 sets a puncturable region on a body surface image extending from the body surface to the set puncture target in the acquired volume data. For example, the puncturable region setting unit 314 can set a puncturable region on the body surface image from a puncture needle reachable range with a puncturable depth of a puncture needle to be used being a radius around the set puncture target in the acquired volume data. When the puncturable region setting unit 314 sets the puncturable region in the volume data, the puncturable region setting unit 314 stores the volume data with the set puncturable region in the volume data storage unit 330.

The protection target setting unit 316 can set a protection target indicating a region to be protected to a region in the puncture needle reachable range of the subject. For example, the protection target setting unit 316 can display three-dimensional volume data in a volume rendering image, and set the blood vessel or the diaphragm as a protection target. Also, in the case where the blood vessel or the diaphragm can be extracted from the three-dimensional volume data by software or the like, the protection target may be automatically set.

The non-puncturable region setting unit 318 can set a non-puncturable region indicating a region in which puncture cannot be performed to a region in the puncture needle reachable range of the subject. For example, the non-puncturable region setting unit 318 displays three-dimensional volume data in a volume rendering image to set a bone region to the non-puncturable region. Also, in the case where the bone region can be extracted from the three-dimensional volume data by software, the non-puncturable region may be automatically set.

The protection target setting unit 316 and the non-puncturable region setting unit 318 are optional components, and can be set at user's request. Thus, there is no need to always set both the protection target setting unit 316 and the non-puncturable region setting unit 318, but only either of them may be set. When the protection target setting unit 316 and the non-puncturable region setting unit 318 set the protection target or the non-puncturable region, the protection target setting unit 316 and the non-puncturable region setting unit 318 store volume data with the set protection target or non-puncturable region in the volume data storage unit 330.

The puncture route extraction unit 319 extracts a puncture route from the set puncturable region on the body surface image to the puncture target. For example, in the case where the protection target setting unit 316 sets the protection target, the puncture route extraction unit 319 extracts a puncture route from the puncturable region on the body surface image to the puncture target based on a region in a first puncture needle reachable range with the protection target being removed from the region in the puncture needle reachable range.

Also, for example, in the case where the non-puncturable region setting unit 318 sets the non-puncturable region, the puncture route extraction unit 319 extracts a puncture route from the puncturable region on the body surface image to the puncture target based on a region in a second puncture needle reachable range with the non-puncturable region being removed from the region in the puncture needle reachable range. The puncture route extraction unit 319 stores the extracted puncture route in the volume data storage unit 330.

In the case where both the protection target and the non-puncturable region are set, the puncture route extraction unit 319 extracts a puncture route from the puncturable region on the body surface image to the puncture target based on a region in a puncture needle reachable range with the protection target and the non-puncturable region being removed from the region in the puncture needle reachable range.

The safety degree calculation unit 320 calculates a safety degree of the extracted puncture route. For example, the safety degree calculation unit 320 calculates a safety degree based on a positional relationship between each puncture route in a puncture route group and the protection target, the puncture route group being a set of puncture routes connecting the set puncturable region on the body surface image to the puncture target. When the safety degree calculation unit 320 calculates the safety degree of each puncture route, the safety degree calculation unit 320 stores the puncture route and the safety degree thereof in the volume data storage unit 330.

The insertion point candidate region display control unit 322 divides the puncturable regions into groups based on the calculated safety degrees, sets a candidate region of a puncture insertion point for puncturing the puncture target in a puncturable region belonging to a predetermined group, and displays the candidate region on the display unit 346 described later. For example, the insertion point candidate region display control unit 322 displays a candidate region of a puncture insertion point on the display unit 346 based on at least either an area of the puncturable region and a distance of the puncture route with a center of gravity of the puncturable region belonging to the predetermined group being the puncture insertion point. The insertion point candidate region display control unit 322 stores the grouped puncturable regions in the volume data storage unit 330.

The volume data storage unit 330 stores the three-dimensional volume data acquired by the volume data acquisition unit 310. Every time the above described setting is performed in the volume data acquired by the volume data acquisition unit 310, the set volume data and the contents of setting are stored in the volume data storage unit 330.

Next, a configuration of hardware of the workstation 300 according to this embodiment will be described.

Figure 3:
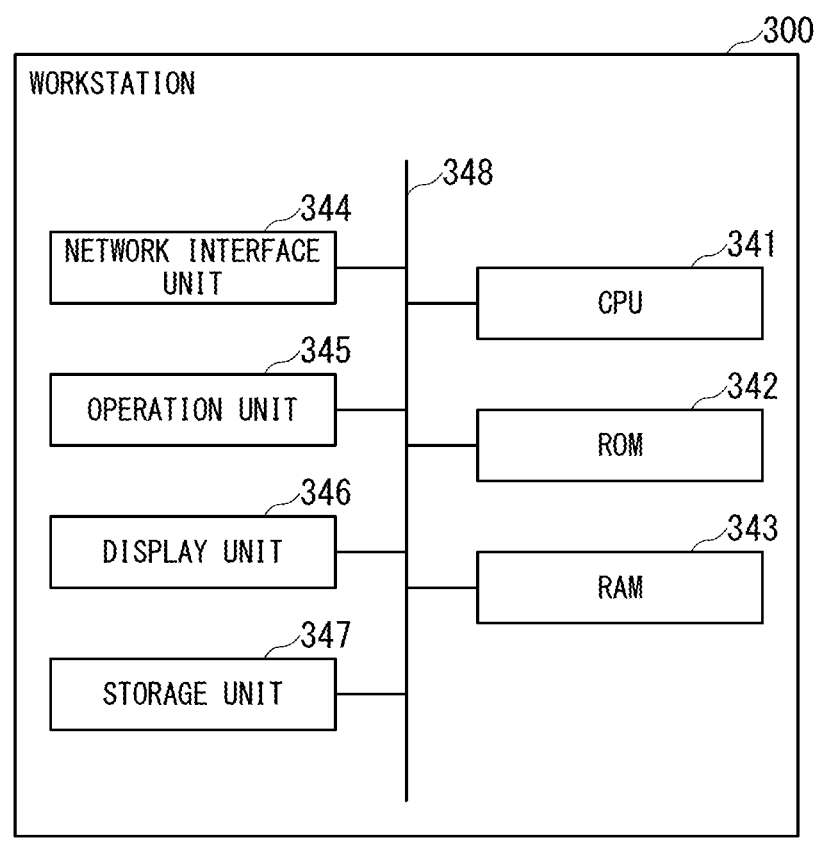
FIG. 3 is a hardware block diagram showing a configuration of the workstation according to the first embodiment.

FIG. 3 is a hardware block diagram showing a configuration of the workstation 300 according to the first embodiment.

As shown in FIG. 3, the workstation 300 includes a CPU (Central Processing Unit) 341, a ROM (Read Only Memory) 342, a RAM (Random Access Memory) 343, a network interface unit 344, an operation unit 345, a display unit 346, a storage unit 347, an internal bus 348, or the like.

The CPU 341 loads various programs stored in the ROM 342 to the RAM 343 and expands the programs, and thus can realize functions of the various programs. The RAM 343 is used as a work area (working memory). The ROM 342 stores various programs. The various programs stored in the ROM 342 include a program for realizing the functions of the workstation 300 shown in FIG. 2.

The network interface unit 344 receives the three-dimensional volume data stored in the storage unit of the image server 200, or receives the volume data from the ultrasonic diagnostic device 400 via the network 500 (FIG. 1).

The operation unit 345 includes an input device or the like that sets a puncture target, a protection target, or a non-puncturable region in the three-dimensional volume data stored in the volume data storage unit 330 in the workstation 300, or inputs, edits, and registers the programs. Specifically, the operation unit 345 includes a pointing device such as a keyboard or a mouse.

The display unit 346 displays the three-dimensional volume data acquired from the image server 200, or a volume rendering image in setting a puncture target, a protection target, or a non-puncturable region. The display unit 346 includes a liquid crystal display or a monitor.

The storage unit 347 constitutes a storage memory, and includes a RAM or a hard disk. In this embodiment, the storage unit 347 constitutes, for example, the volume data storage unit 330 that stores the three-dimensional volume data.

The internal bus 348 is connected to each component so that the CPU 341 controls the entire workstation 300.

As such, in this embodiment, the storage unit 347 constitutes the volume data storage unit 330, and executes the programs stored in the ROM 342, thereby realizing the functions of the workstation 300 shown in FIG. 2.

(Puncture Insertion Point Display Process)

Next, an operation of a puncture insertion point display process by the workstation 300 according to the first embodiment will be described.

Figure 4:
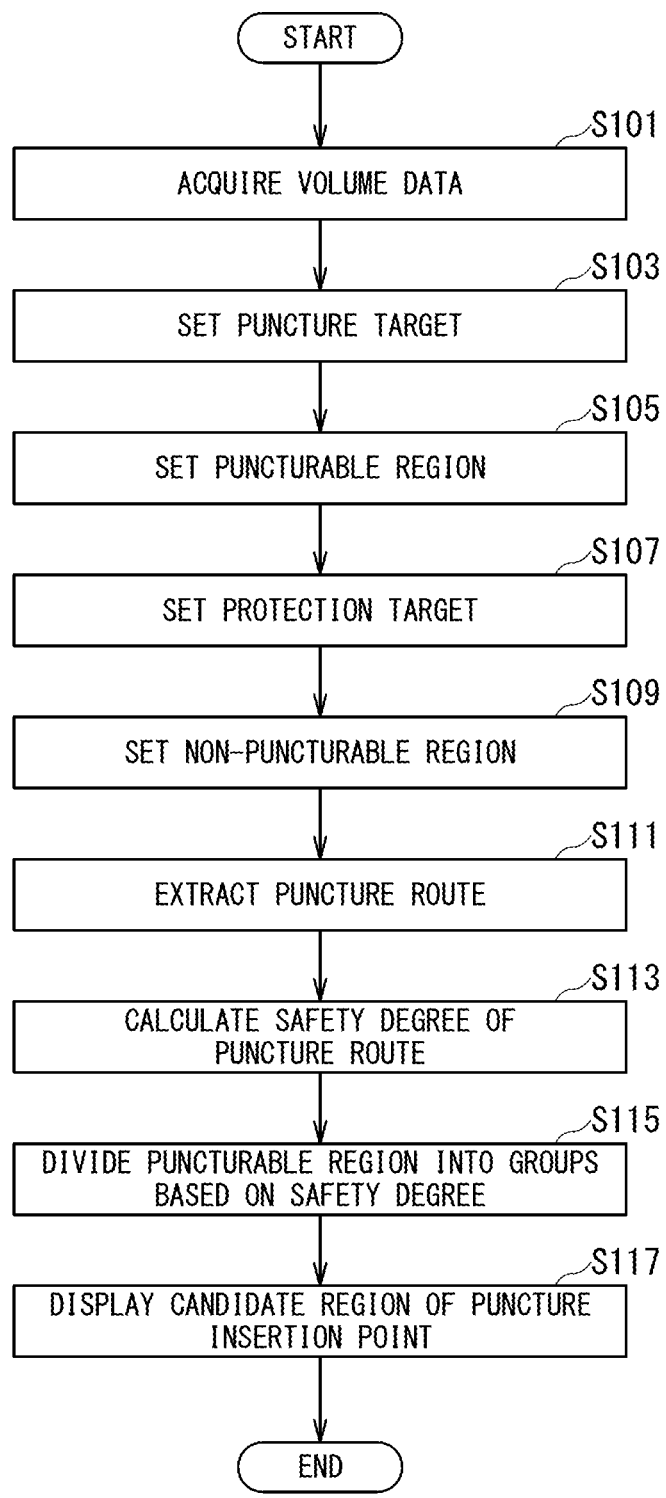
FIG. 4 is a flowchart showing a puncture insertion point display process in which the workstation according to the first embodiment displays a candidate region of a puncture insertion point on a body surface image.

FIG. 4 is a flowchart showing a puncture insertion point display process in which the workstation 300 according to the first embodiment displays a candidate region of a puncture insertion point on the body surface image. In FIG. 4, numerals with S refer to steps in the flowchart.

First in step S101, the volume data acquisition unit 310 acquires three-dimensional volume data from the image server 200 via the network 500. The volume data acquisition unit 310 stores the acquired three-dimensional volume data in the volume data storage unit 330.

In step S103, the puncture target setting unit 312 sets a puncture target in the acquired volume data.

In step S105, the puncturable region setting unit 314 sets a puncturable region on the body surface image from a puncture needle reachable range with a puncturable depth of a puncture needle to be used being a radius around a set puncture target.

Figure 5B:
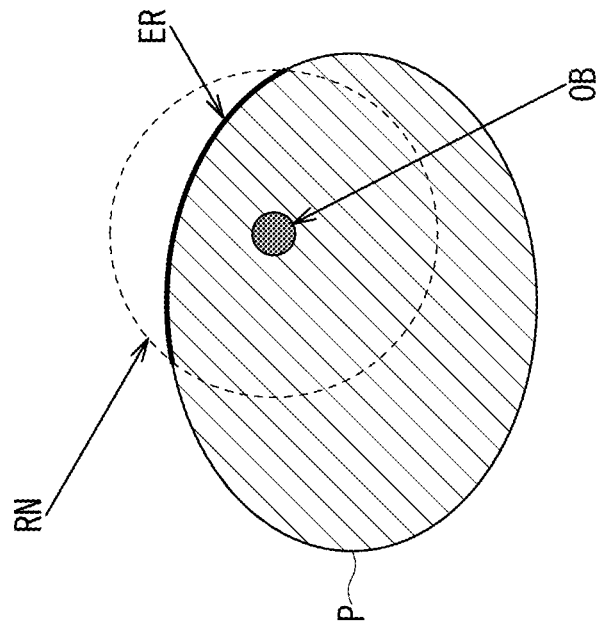
FIGS. 5A and 5B illustrate a case where a puncture target setting unit in the workstation according to the first embodiment sets a puncturable region on the body surface image.
Figure 5A:
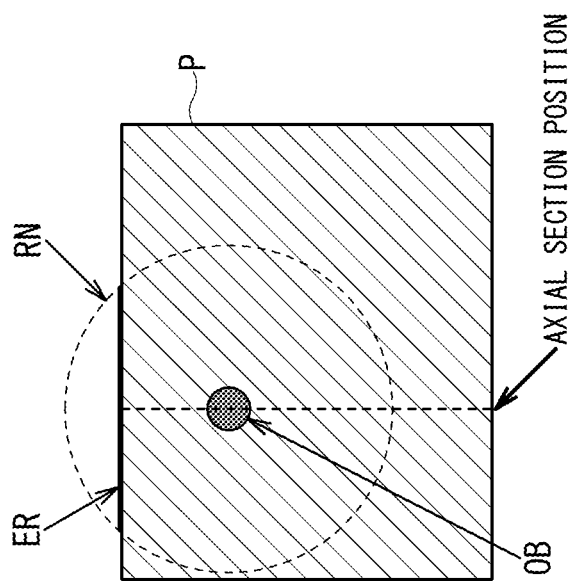

FIGS. 5A and 5B illustrate a case where the puncture target setting unit 312 in the workstation 300 according to the first embodiment sets the puncturable region on the body surface image.

FIG. 5A shows a picked-up image of a subject P in a sagittal section. FIG. 5B shows the picked-up image of the subject P in an axial section. In the sagittal sectional image shown in FIG. 5A, the head of the subject P is located on the left of the sheet (FIG. 5A), and the feet of the subject P are located on the right of the sheet (FIG. 5A).

The axial sectional image shown in FIG. 5B shows a sectional image in an axial section position in FIG. 5A, and the feet are located on the back of the sheet (FIG. 5B), and the head is located on the front of the sheet (FIG. 5B).

In the examples in FIGS. 5A and 5B, a puncture target OB is set for three-dimensional volume data. The puncturable region setting unit 314 sets a puncturable region ER on a body surface image of the subject P from a puncture needle reachable range RN with a puncturable depth of a puncture needle to be used being a radius around the puncture target OB.

As an example, a method of extracting a puncture route from the set puncturable region ER on the body surface image to the puncture target OB will be described.

Figure 6B:
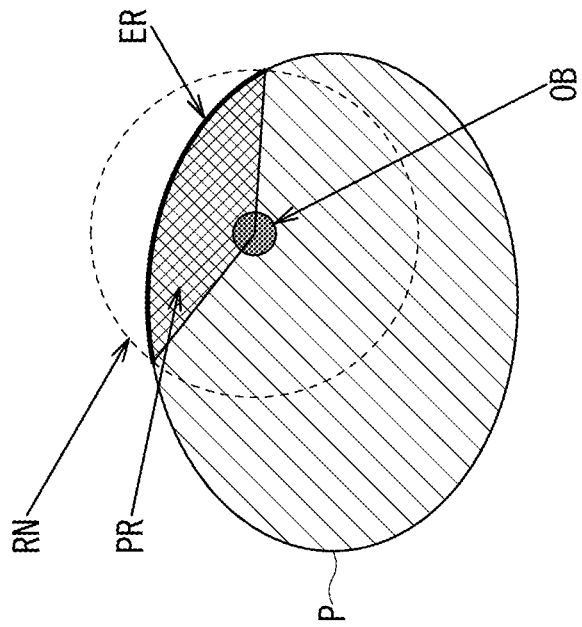
FIGS. 6A and 6B illustrate a method for a puncture route extraction unit in the workstation according to the first embodiment to extract a puncture route.
Figure 6A:
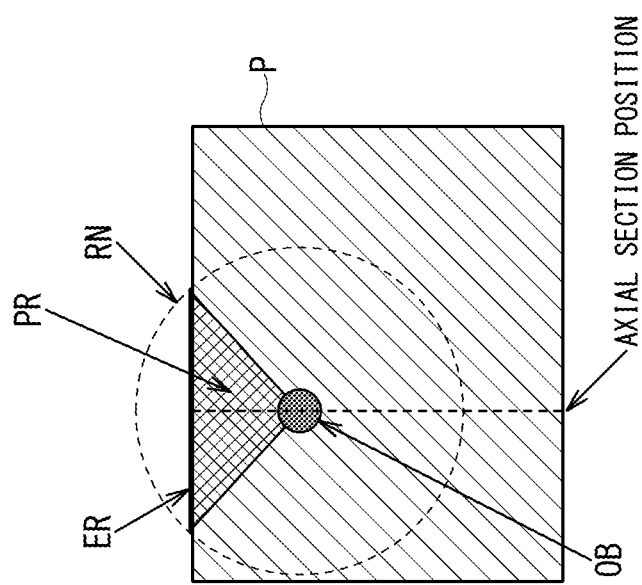

FIGS. 6A and 6B illustrate a method for the puncture route extraction unit 319 in the workstation 300 according to the first embodiment to extract a puncture route.

FIGS. 6A and 6B show the contents in FIGS. 5A and 5B with a puncture route group PR being added. Specifically, the puncture route extraction unit 319 extracts substantially linear puncture routes from the puncturable region ER to the puncture target OB, and displays a set of the puncture routes as the puncture route group PR. Specifically, the puncture route group PR indicates that the puncture route extraction unit 319 extracts puncture routes and there are a plurality of puncture routes around the puncture target OB.

FIG. 6A corresponds to FIG. 5A, and FIG. 6B corresponds to FIG. 5B. The puncture routes have a three-dimensional positional relationship.

In step S107 (FIG. 4), the protection target setting unit 316 can set a protection target indicating a region to be protected to a region in the puncture needle reachable range RN of the subject P.

In step S109, the non-puncturable region setting unit 318 can set a non-puncturable region indicating a region in which puncture cannot be performed to the region in the puncture needle reachable range RN of the subject P.

In step S111, the puncture route extraction unit 319 extracts a puncture route from the puncturable region ER on the body surface image to the puncture target OB.

The puncture routes extracted by the puncture route extraction unit 319 in the case where the protection target and the non-puncturable region are set as described in steps S107 and S109 will be described with reference to the drawings.

Figure 7:
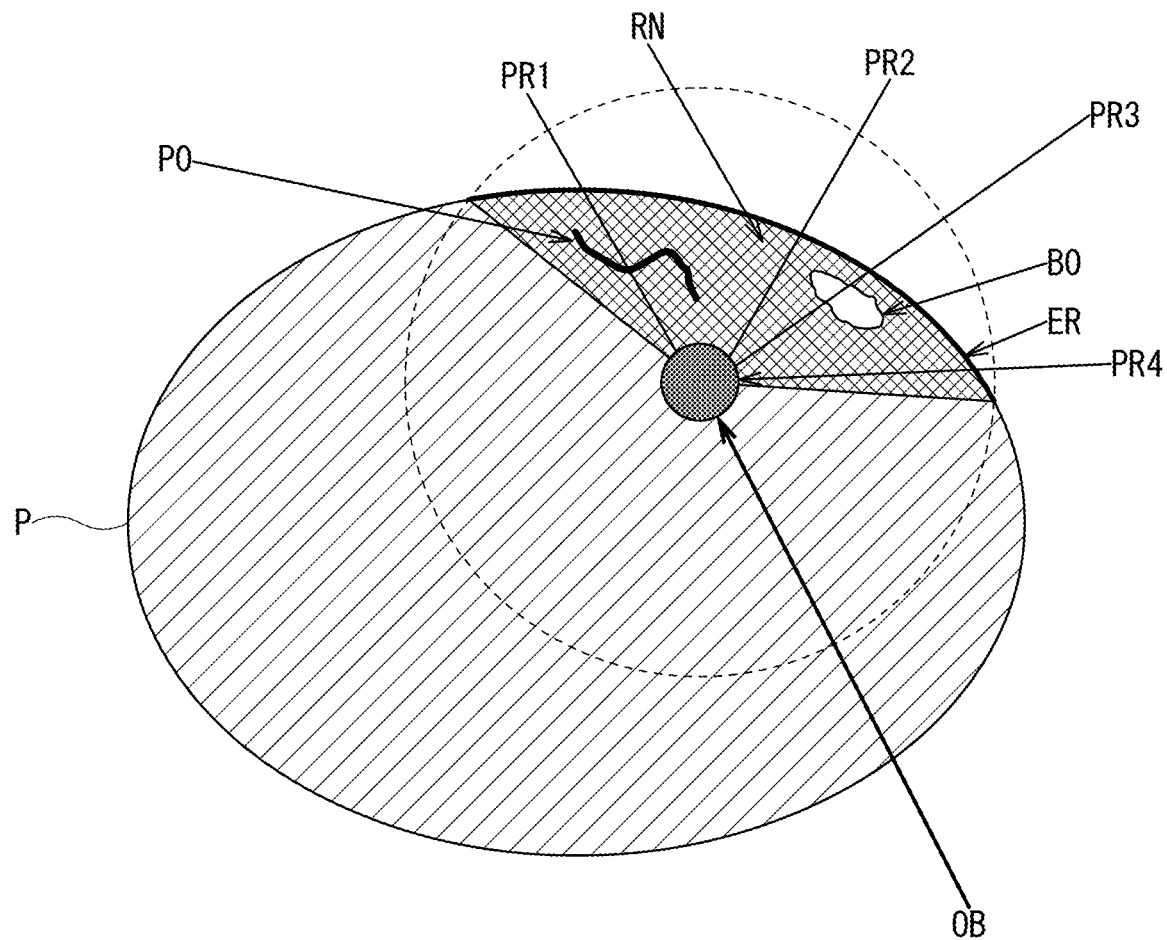
FIG. 7 illustrates a method for the puncture route extraction unit in the workstation according to the first embodiment to extract a puncture route from a puncturable region to a puncture target.

FIG. 7 illustrates a method for the puncture route extraction unit 319 in the workstation 300 according to the first embodiment to extract the puncture routes from the puncturable region ER to the puncture target OB. FIG. 7 shows an axial section, but the puncture routes have a three-dimensional positional relationship around the puncture target OB.

As shown in FIG. 7, in the puncture needle reachable range RN of the subject P, a protection target PO indicating the blood vessel as a protection target and a bone region BO indicating a non-puncturable region are set. In the example in FIG. 7, there is the protection target PO indicating the blood vessel in a puncture route PR1. Thus, the puncture route PR1 is an unsafe route. On the other hand, there is no interruption in a puncture route PR2 and a puncture route PR4 in the puncture needle reachable range RN. Thus, the puncture route PR2 and the puncture route PR4 are safe routes. In a puncture route PR3, there is the bone region BO indicating the non-puncturable region. Thus, the puncture route PR3 is a non-puncturable route in which puncture cannot be performed.

Thus, the puncture route extraction unit 319 extracts a substantially linear safe puncture route from the puncturable region ER to the puncture target OB without any interruption in the puncture route such as the protection target PO or the bone region BO in the region in the puncture needle reachable range RN of the subject P.

In step S113 (FIG. 4), the safety degree calculation unit 320 calculates a safety degree of the extracted puncture route.

Specifically, the safety degree calculation unit 320 calculates a safety degree based on a positional relationship between each puncture route of a puncture route group and a protection target, the puncture route group being a set of puncture routes connecting the puncturable region ER on the body surface image to the puncture target OB.

As an example, a safety degree calculation method for the safety degree calculation unit 320 to calculate a safety degree of the puncture route from the puncturable region ER to the puncture target OB will be described.

Figure 8:
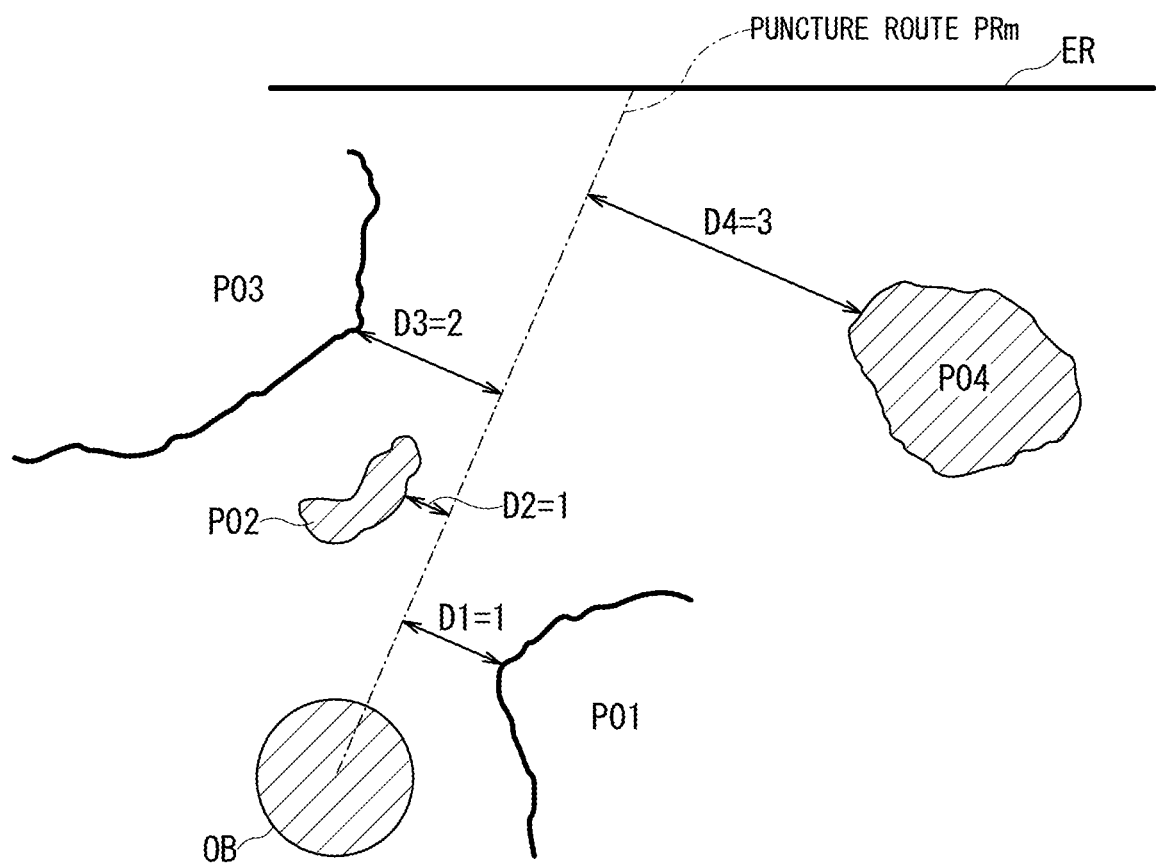
FIG. 8 illustrates a safety degree calculation method for a safety degree calculation unit in the workstation according to the first embodiment to calculate a safety degree of the puncture route from the puncturable region to the puncture target.

FIG. 8 illustrates a safety degree calculation method for the safety degree calculation unit 320 in the workstation 300 according to the first embodiment to calculate a safety degree of the puncture route from the puncturable region ER to the puncture target OB.

As shown in FIG. 8, a puncture route PRm indicates the puncture route from the puncturable region ER to the puncture target OB, and safety degrees are calculated from distances from protection targets (PO1 to PO4) to the puncture route PRm. For example, in the puncture route PRm, the lowest value of a safety degree of all the safety degrees of the protection targets (PO1 to PO4) can be adopted as a value indicating the safety degree of the puncture route.

In FIG. 8, thresholds are assigned depending on the distances from the puncture route to the protection targets. For example, when the distance from the puncture route is less than 1 cm, the safety degree is set to "1", when the distance from the puncture route is 1 cm to less than 2 cm, the safety degree is set to "2", and when the distance from the puncture route is 2 cm to less than 3 cm (or 2 cm or more), the safety degree is set to "3".

In the case in FIG. 8, since the protection target PO1 is at the distance of less than 1 cm from the puncture route PRm, a safety degree D1 is "1", and since the protection target PO2 is also at the distance of less than 1 cm from the puncture route PRm, a safety degree D2 is "1". Since the protection target PO3 is at the distance of 1 cm to less than 2 cm from the puncture route PRm, a safety degree D3 is "2", and since the protection target PO4 is at the distance of 2 cm or more from the puncture route PRm, a safety degree D4 is "3". Thus, in the case of the example 1, the safety degree of the puncture route PRm is "1".

The calculation method of the safety degree is not limited to this. For example, a general safety degree may be calculated from the safety degrees of all the protection targets (PO1 to PO4). Specifically, the reciprocal of the safety degree of each protection target is taken to obtain an unsafety degree of each protection target, and calculate the sum of the unsafety degrees. Then, the reciprocal of the sum of the unsafety degrees is taken to obtain a general safety degree.

When the general safety degree is calculated, the threshold may be used for determination. When the safety degree is calculated, the distance may be directly applied to calculate the safety degree. The distance or the threshold may be weighted as appropriate.

For example, the blood vessel has a higher safety degree than the diaphragm or the heart, and thus the distance is multiplied by a safety degree calculation coefficient larger than one so that the safety degree of the blood vessel is relatively higher than the safety degree of the diaphragm or the heart.

In this case, the diaphragm or the heart has a lower safety degree than the blood vessel, and thus the distance is multiplied by a safety degree coefficient smaller than the safety degree calculation coefficient of the blood vessel so that the safety degree of the diaphragm or the heart is relatively lower than the safety degree of the blood vessel.

Figure 9:
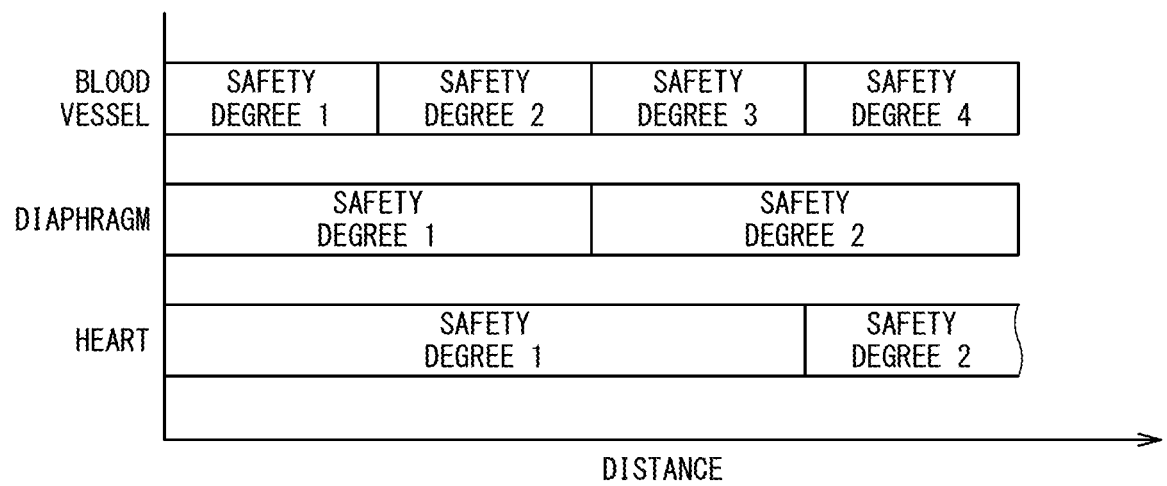
FIG. 9 illustrates a safety degree of each protection target in the case where the safety degree calculation unit in the workstation according to the first embodiment weights a distance.

FIG. 9 shows the safety degree of each protection target in the case where the safety degree calculation unit 320 (FIG. 2) in the workstation according to the first embodiment weights the distance.

In FIG. 9, as an example, in the case where the protection targets are the blood vessel, the diaphragm, and the heart, the safety degree calculation unit 320 multiplies each distance from the puncture route by a predetermined safety degree calculation coefficient and weights the distance to calculate the safety degree for the distance of each protection target. For example, for the blood vessel, the distance is weighted so that the safety degree is about twice higher than that of the diaphragm, and about three times higher than that of the heart.

Thus, in FIG. 9, even with the same distance from the puncture route to the protection targets, the safety degree calculation unit 320 indicates that the protection targets have different safety degrees, and that the distance is weighted so that safety degree 1<safety degree 2<safety degree 3<safety degree 4.

In this embodiment, to calculate the safety degree, the safety degree calculation unit 320 may use the unsafety degree as the reciprocal of the safety degree to indicate the safety degree of the puncture route.

Figure 10:
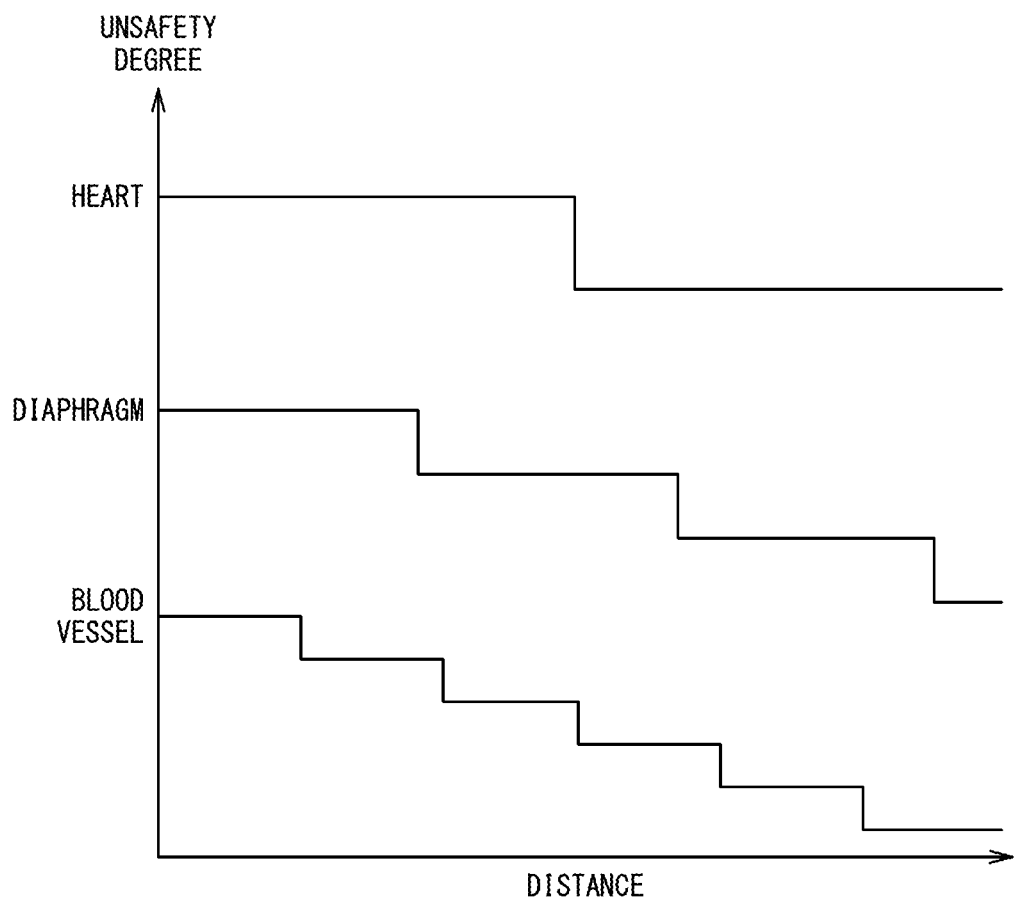
FIG. 10 illustrates a case where the safety degree calculation unit in the workstation according to the first embodiment weights the distance using an unsafety degree.

FIG. 10 illustrates a case where the safety degree calculation unit 320 (FIG. 2) in the workstation according to the first embodiment uses the unsafety degree to weight the distance.

FIG. 10 shows unsafety degrees of the protection targets with respect to the distance in the case where, as an example, the safety degree calculation unit 320 weights the distance as in FIG. 9. In this case, the heart has a higher unsafety degree than the diaphragm and the blood vessel, and the diaphragm has a higher unsafety degree than the blood vessel. The unsafety degree is represented by the reciprocal of the safety degree, and is inversely proportional to the safety degree.

In step S115 (FIG. 4), the insertion point candidate region display control unit 322 divides the puncturable region ER into groups based on the calculated safety degrees, and displays the safety degrees of puncture in different colors on the body surface image. For example, the safety degrees are displayed in different colors on the body surface image in such a manner that a high safety degree region with a high safety degree is blue, a middle safety degree region with a middle safety degree is yellow, a high unsafety degree region with a high unsafety degree (low safety degree) is red, and a non-puncturable region in which puncture cannot be performed is gray, or the like.

Figure 11:
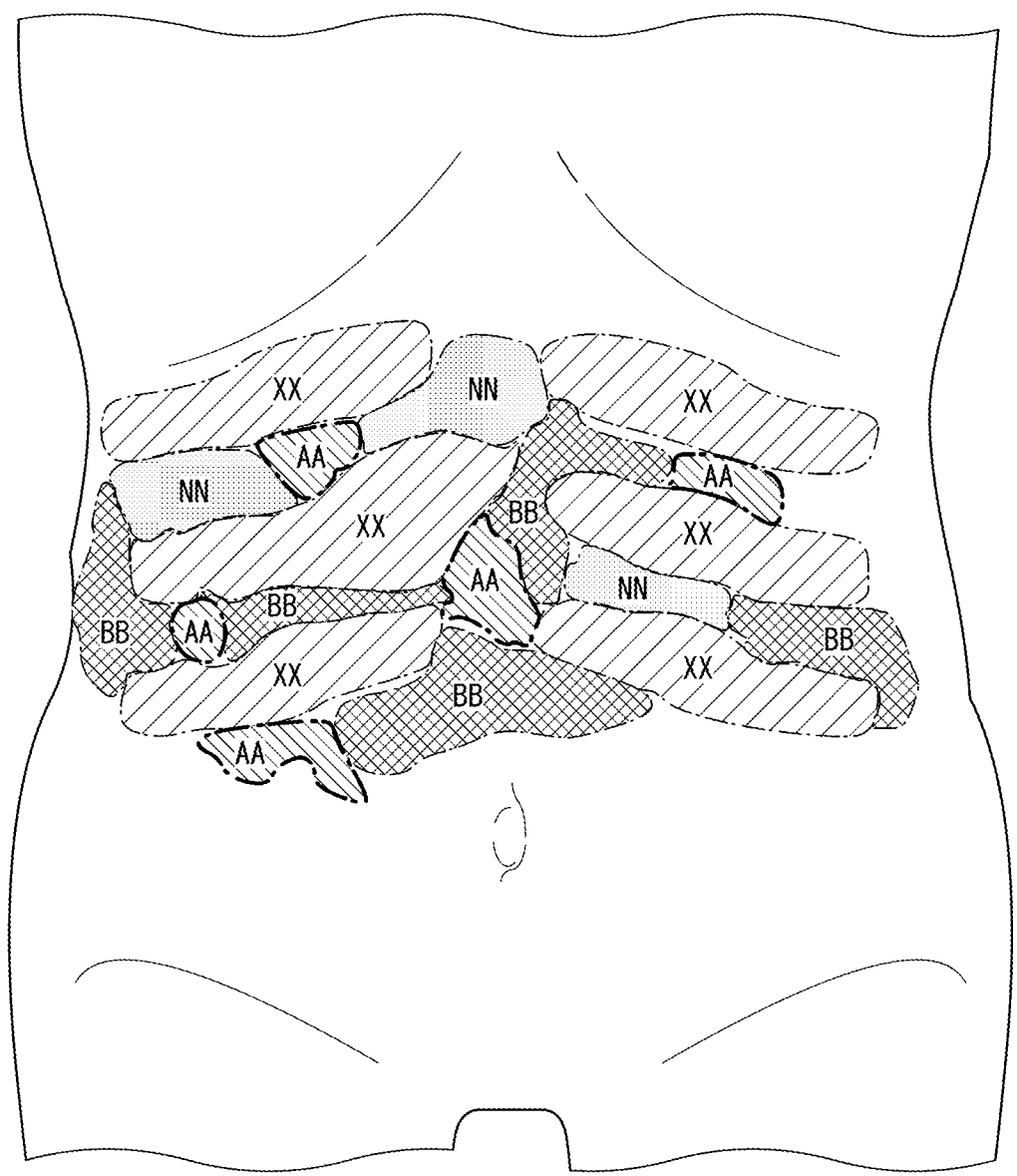
FIG. 11 illustrates a case where an insertion point candidate display control unit in the workstation according to the first embodiment displays a safety degree map displaying safety degrees in different colors on the body surface image to be a display unit.
Figure 11:
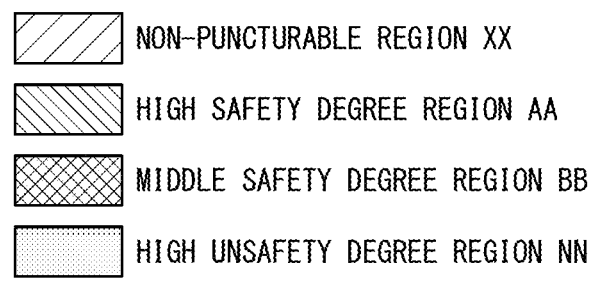

FIG. 11 illustrates a case where the insertion point candidate region display control unit 322 in the workstation 300 according to the first embodiment displays a safety degree map displaying the safety degrees in different colors on the body surface image to be the display unit 346.

As shown in FIG. 11, the insertion point candidate region display control unit 322 displays, on the body surface image, a high safety degree region AA with a high safety degree in blue, a middle safety degree region BB with a middle safety degree in yellow, a high unsafety degree region NN with a high unsafety degree (low safety degree) in red, and a non-puncturable region XX in which puncture cannot be performed in gray.

In the example in FIG. 11, the high unsafety degree region NN with a high unsafety degree (low safety degree) indicates a region including protection targets such as the heart, the diaphragm, and the blood vessel, and the non-puncturable region XX in which puncture cannot be performed indicates a non-puncturable region such as a bone region.

In step S117 (FIG. 4), the insertion point candidate region display control unit 322 displays a candidate region of a puncture insertion point for puncturing the puncture target in a puncturable region belonging to a predetermined group. For example, the insertion point candidate region display control unit 322 extracts a puncture insertion candidate region from the puncturable region belonging to the group of the high safety degree region AA with a high safety degree, sets the center of gravity of the puncture insertion candidate region to a puncture insertion point, and displays the candidate region of the puncture insertion point (that is, the puncture insertion candidate region) in the order of scores based on at least either an area of each puncture insertion candidate region or a distance of the puncture route.

Figure 12:
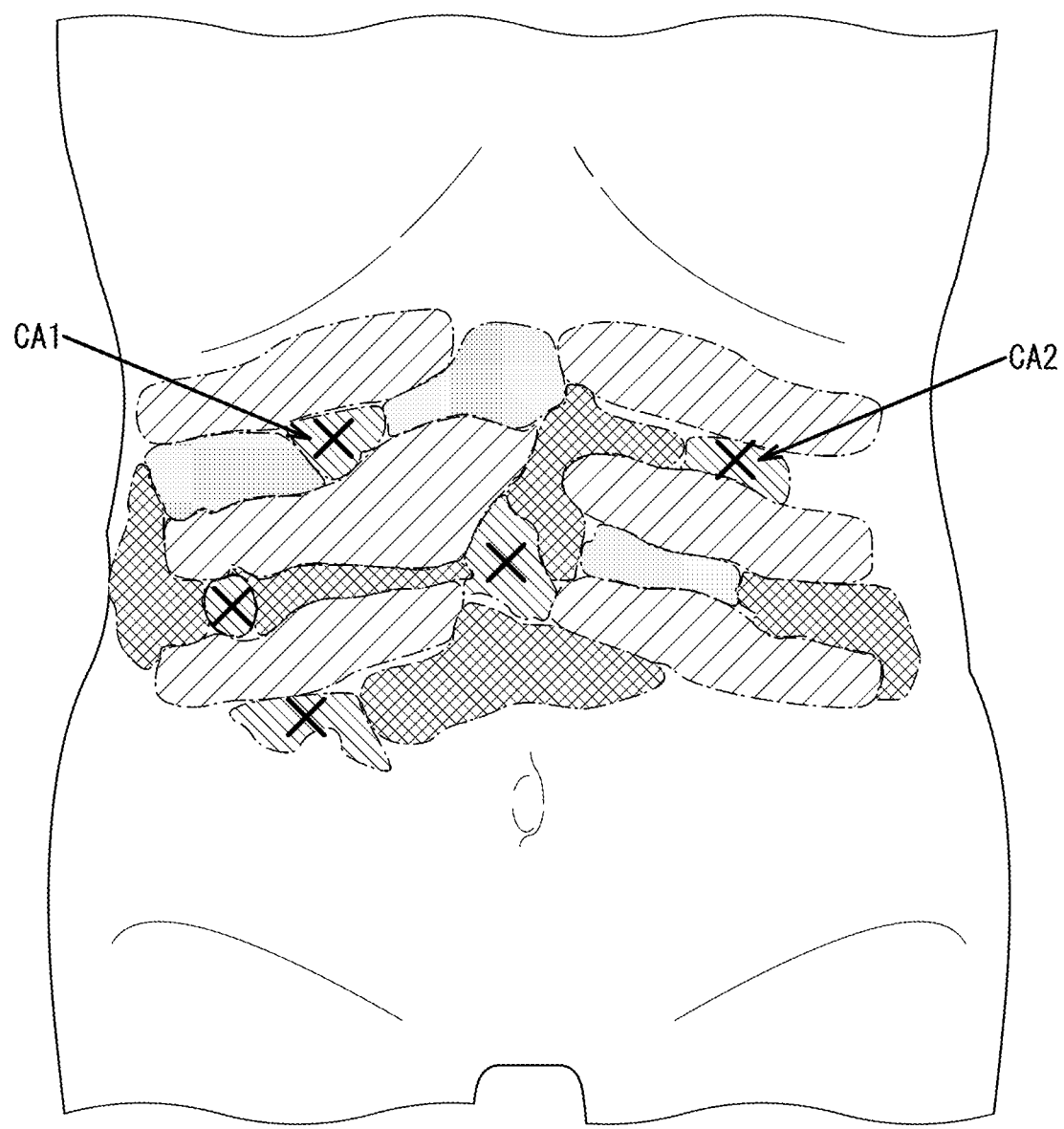
FIG. 12 illustrates a case where the insertion point candidate display control unit in the workstation according to the first embodiment displays a puncture insertion point in a puncture insertion candidate region on the body surface image.

FIG. 12 illustrates a case where the insertion point candidate region display control unit 322 in the workstation 300 according to the first embodiment displays the puncture insertion point of the puncture insertion candidate region on the body surface image.

As shown in FIG. 12, the insertion point candidate region display control unit 322 displays puncture insertion candidate regions CA1, CA2 and puncture insertion points thereof on the body surface image from the group of the high safety degree region AA based on at least either the area of each puncturable region or the distance of the puncture route.

When the area of the puncturable region is relatively large, it is considered that the risk of damaging the protection target is low even with an error in the puncture insertion point between puncture planning and actual puncture. Also, when the distance of the puncture route from the puncture insertion point to the puncture target is relatively short, the depth of the puncture is small, and it is considered that burden on both the operator and the subject is reduced.

Thus, for example, adjacent points are connected of the set of points in the group of the high safety degree region AA in the puncturable region ER, and divided into a plurality of clusters. The insertion point candidate region display control unit 322 handles each cluster as a puncture insertion candidate region (for example, CA1, CA2), and calculates an area of each puncture insertion candidate region, and a distance from the center of gravity of each puncture insertion candidate region to the puncture target OB.

Then, the insertion point candidate region display control unit 322 assigns a high score when the calculated area of the puncture insertion candidate region is relatively large, while assigns a low score when the area of the puncture insertion candidate region is relatively small. The insertion point candidate region display control unit 322 assigns a high score when the distance from the center of gravity of the puncture insertion candidate region to the puncture target is relatively short, while assigns a low score when the distance from the center of gravity of the puncture insertion candidate region to the puncture target is relatively long.

As such, the insertion point candidate region display control unit 322 can provide the operator the puncture insertion candidate region in the order of scores based on at least either the area of each puncture insertion candidate region or the distance from the center of gravity of each puncture insertion candidate region to the puncture target.

In FIG. 12, a puncture insertion candidate region with the highest store is displayed as the puncture insertion candidate region CA1, and a puncture insertion candidate region with the second highest score is displayed as the puncture insertion candidate region CA2. The insertion point candidate region display control unit 322 provides the operator the center of gravity of each puncture insertion candidate region as a puncture insertion point (X in FIG. 12).

As described above, the workstation 300 according to this embodiment acquires the three-dimensional volume data from the image server 200 via the network 500, and sets the puncture target OB in the volume data. The workstation 300 can set the protection target PO and the non-puncturable region (bone region BO) in the volume data, and extract the puncture route from the puncturable region ER to the puncture target OB. The workstation 300 calculates the safety degree of the extracted puncture route, divides the puncturable region into groups based on the calculated safety degrees, and displays the candidate region of the puncture insertion point for puncturing the puncture target in the puncturable region belonging to the predetermined group.

As such, the workstation 300 according to this embodiment can display the candidate region of the puncture insertion point (that is, the puncture insertion candidate region) in the puncturable region belonging to the predetermined group. Thus, the operator can easily have a look at the candidate regions of the plurality of puncture insertion points with a high safety degree on the body surface image, and can select a puncture insertion point for the safest puncture among the candidate regions of the plurality of puncture insertion points.

In the workstation 300 according to this embodiment, the protection target setting unit 316 and the non-puncturable region setting unit 318 set the protection target PO and the non-puncturable region (bone region BO), and then the safety degree calculation unit 320 calculates the safety degree, but this embodiment is not limited to this.

For example, in the case where the protection target setting unit 316 and the non-puncturable region setting unit 318 do not set the protection target PO nor the bone region BO, the puncture route extraction unit 319 may extract the puncture route from the puncturable region ER on the body surface image to the puncture target OB, and the safety degree calculation unit 320 may calculate the safety degree depending on only the distance to the puncture target OB in the extracted puncture route.

Second Embodiment

In the first embodiment described above, the insertion point candidate region display control unit 322 in the workstation 300 according to this embodiment displays the candidate region of the puncture insertion point (that is, the puncture insertion candidate region) on the body surface image based on at least either the area of the puncturable region belonging to the group of the high safety degree region AA or the distance of the puncture route.

In the second embodiment, in addition to the first embodiment, an operator uses an operation unit 345 (virtual puncture accepting unit) to designate a candidate region of a puncture insertion point displayed on a body surface image, and then puncture support information relating to the candidate region of the puncture insertion point is displayed on a display unit 346.

The puncture support information includes information relating to the puncture insertion point or the puncture insertion candidate region, and refers to information in which a puncture route from a puncture insertion point to a puncture target or a sectional image are displayed on an image other than the body surface image (for example, FIG. 12). Next, the second embodiment will be described with reference to the drawing.

Figure 13:
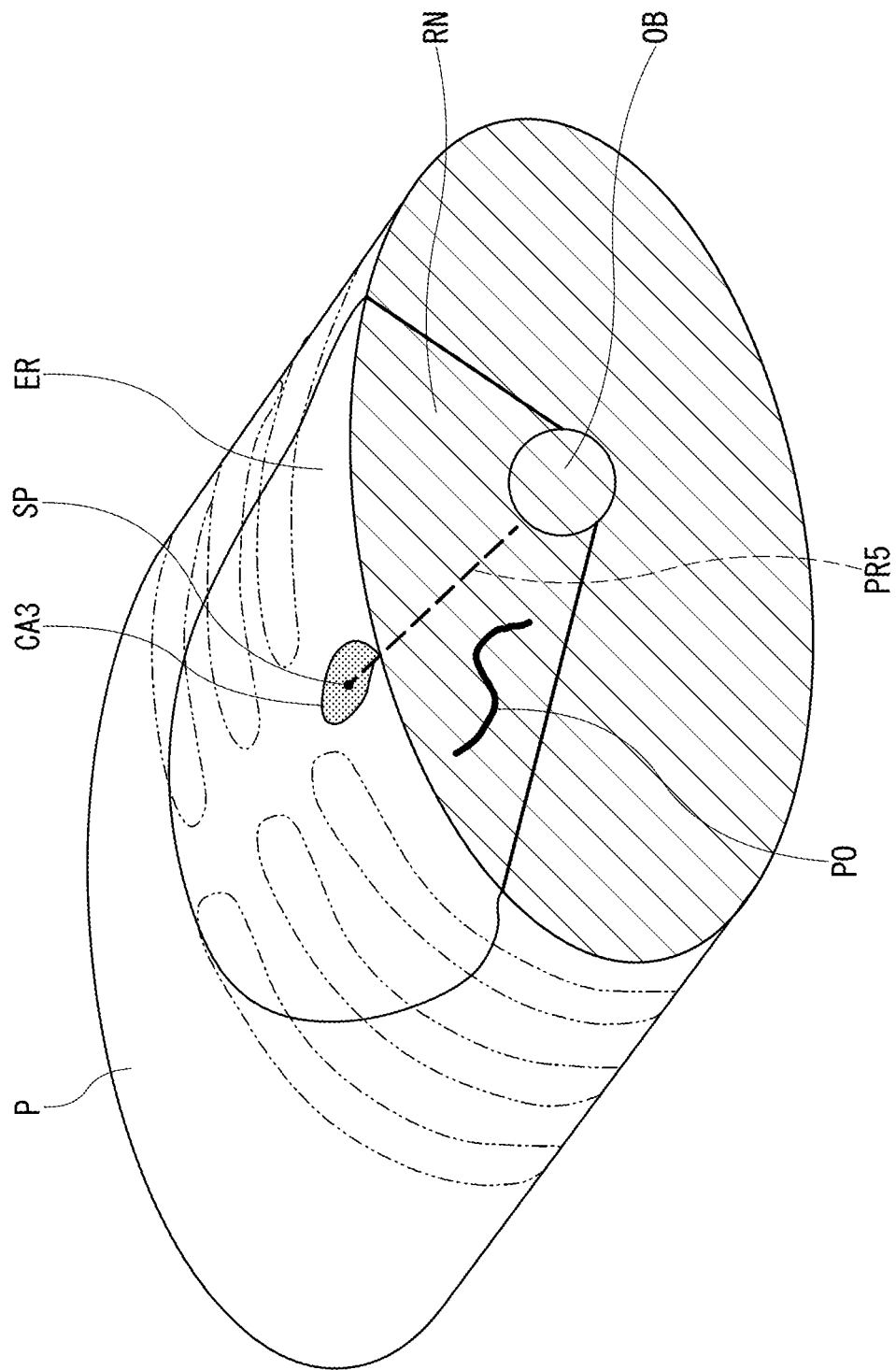
FIG. 13 illustrates a case where a workstation according to a second embodiment displays puncture support information relating to a designated puncture insertion point (or a puncture insertion candidate region) on a display unit.

FIG. 13 illustrates a case where a workstation 300 according to the second embodiment displays puncture support information relating to a designated puncture insertion point (or puncture insertion candidate region) on the display unit 346. The same components are denoted by the same reference numerals, and descriptions thereof will be omitted.

As shown in FIG. 13, when the operator designates a puncture insertion point SP or a puncture insertion candidate region CA3 on a body surface image of a subject P, a sectional image including a puncture route PR5 connecting the puncture insertion point SP and the puncture target OB is displayed as puncture support information. In this case, if the sectional image includes a protection target PO on which calculation of a safety degree is based in calculating the safety degree, the sectional image including the protection target PO is automatically selected and displayed on the display unit 346.

In this case, an assumed virtual puncture route may be displayed by graphic display, and the protection target PO may be highlighted. The sectional image in the second embodiment is not restrictively displayed in a volume rendering image as in FIG. 13, but may be displayed two-dimensionally.

As such, the operator may easily visually check the puncture insertion point SP in the puncture insertion candidate region CA3 displayed on the body surface image, and also the sectional image in puncture from the puncture insertion point SP. This allows an optimum puncture insertion point or puncture insertion candidate region to be selected and determined.

Third Embodiment

In the first embodiment described above, the insertion point candidate region display control unit 322 in the workstation 300 displays the candidate region of the puncture insertion point (that is, the puncture insertion candidate region) for puncturing the puncture target in the puncturable region belonging to the predetermined group. Also, in the second embodiment, the puncture support information (for example, sectional image) corresponding to the puncture insertion point SP is displayed.

In the third embodiment, in addition to the first and second embodiments, a projector (projection device) is further provided that projects, on a subject P, a puncturable region ER on a body surface image. Thus, an insertion point candidate region display control unit 322 (FIG. 2) can use the projector to directly project a candidate region of a puncture insertion point (that is, a puncture insertion candidate region) on a body surface of the subject P. The third embodiment will be described with reference to the drawings.

Figure 14:
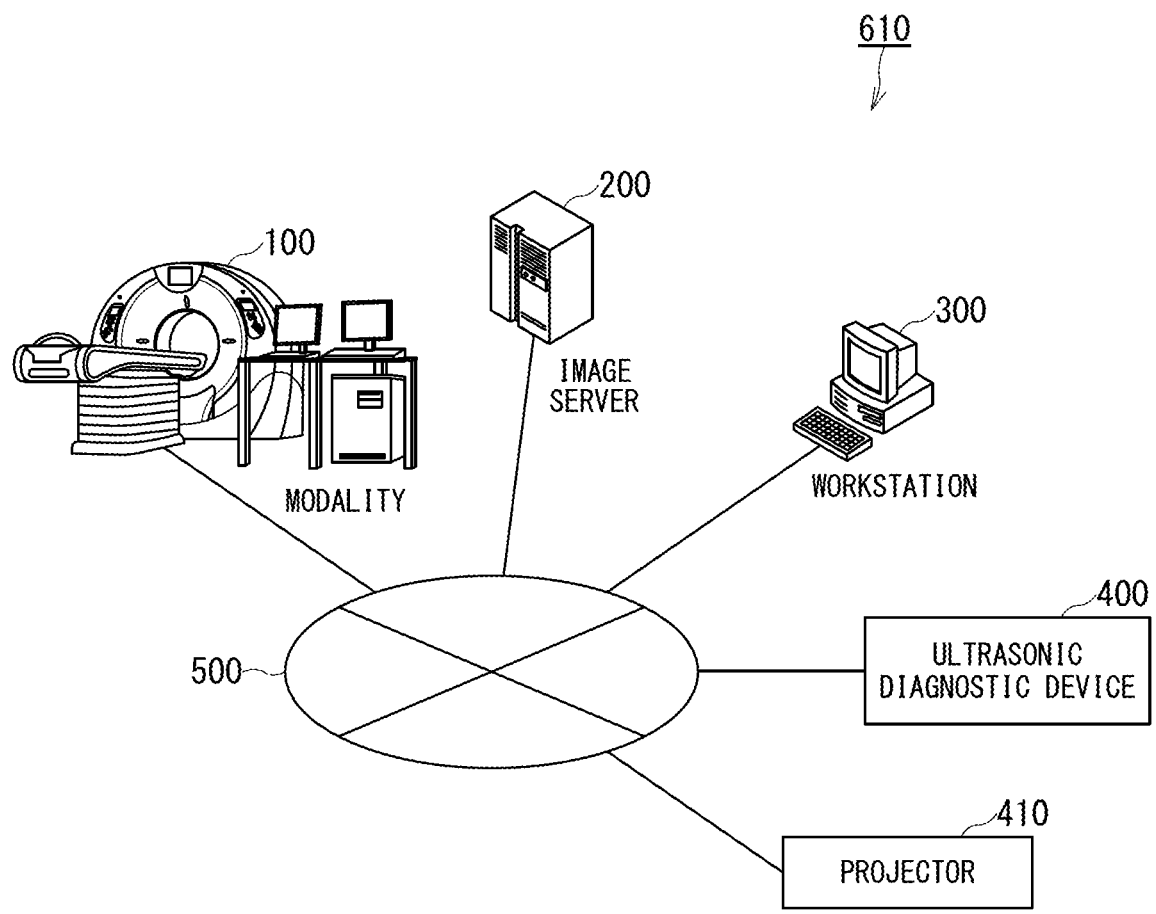
FIG. 14 is a schematic configuration diagram showing an example of a schematic configuration of a puncture system using a workstation according to a third embodiment.

FIG. 14 is a schematic configuration diagram showing an example of a schematic configuration of a puncture system 610 using the workstation 300 according to the third embodiment.

As shown in FIG. 14, the puncture system 610 includes a modality 100, an image server 200, a workstation 300, an ultrasonic diagnostic device 400, a projector 410, a network 500, or the like. The third embodiment is different from the first embodiment in further including the projector 410. Thus, the same components as in the first embodiment are denoted by the same reference numerals and descriptions thereof will be omitted.

The projector 410 projects, on the subject P, for example, a puncturable region on the body surface image or three-dimensional volume data or a sectional image displayed on a display unit 346 in the workstation 300.

Figure 15:
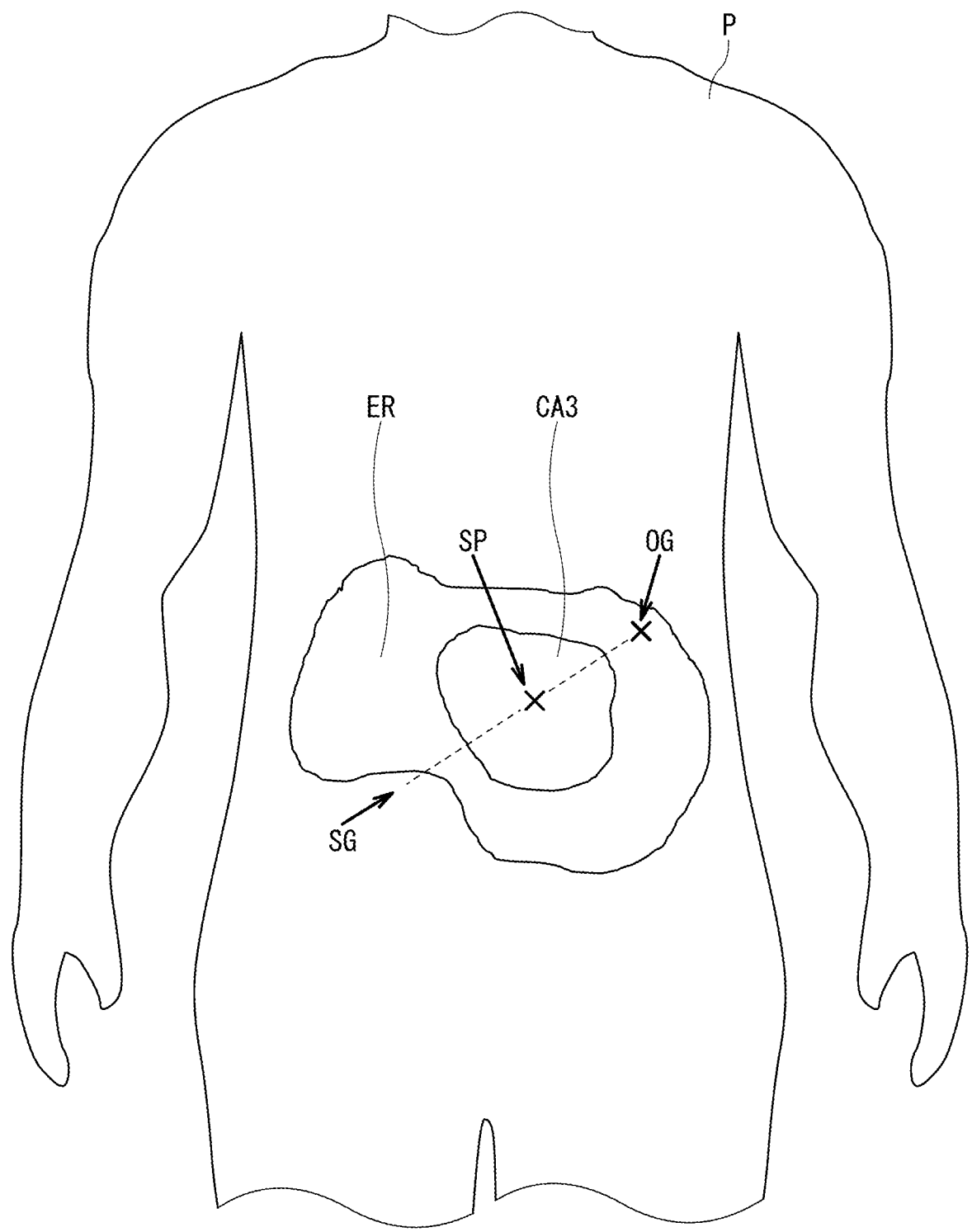
FIG. 15 illustrates a case where an insertion point candidate display unit in the workstation according to the third embodiment uses a projector (not shown) to project a candidate of a puncture insertion point shown in FIG. 11 on a body surface of a subject.

FIG. 15 illustrates a case where the insertion point candidate region display control unit 322 in the workstation 300 according to the third embodiment uses the projector 410 to project the candidate region of the puncture insertion point shown in FIG. 13 on the body surface of the subject P. The same components as in FIG. 13 are denoted by the same reference numerals, and descriptions thereof will be omitted.

In FIG. 15, the puncturable region ER including a puncture insertion candidate region CA3 shown in FIG. 13 is projected on the body surface of the subject P, and the puncture insertion point SP and an insertion direction guide SG are projected.

The insertion direction guide SG refers to a projected insertion direction into the puncture insertion point SP, and a puncture target guide OG refers to a puncture target OB (FIG. 13) projected on the body surface.

In the third embodiment, puncture insertion candidate regions CA1, CA2 (FIG. 12) may be projected, and the insertion point candidate region display control unit 322 may project a high unsafety degree region NN with a high unsafety degree or a non-puncturable region XX in which puncture cannot be performed.

Thus, for example, a misalignment of a non-puncturable region XX due to the costa from the actual costa may be visually corrected. A feature such as the epigastric fossa as an example of the xiphisternum may be specified in three-dimensional volume data for puncture planning, and the feature may be projected on the body surface to visually correct the misalignment.

In the third embodiment, the projected information is not limited to the above, but for example, a depth from the body surface to the puncture target OB may be represented by a length, or an insertion angle may be projected on the body surface. In this case, the length and the insertion angle may be represented by numerical values, or the length may be artificially projected, or the insertion angle may be artificially projected.

In the first to third embodiments, for example, in the case where the puncture insertion point SP is determined from the plurality of puncture insertion points, and the ultrasonic diagnostic device 400 can be automatically placed on the subject P from the positional information on the puncture insertion point SP and the puncture target OB, the ultrasonic diagnostic device 400 may be automatically placed.

Although a couple of embodiments of the invention are explained, these embodiments are exemplary only and it is not intended that the scope of the invention is limited by the embodiments. These embodiments can be put into practice in other various forms, and can be variously omitted, replaced or changed within the scope of the invention. The embodiments and their modifications are included in the scope and the coverage of the invention, and similarly in the equivalents to the claimed invention.

Also, in the embodiments of the present invention, the steps of flow charts show example processes that are performed in time-series in the order described, but they may also include processes that can be performed in parallel or independently rather than being performed in time-series.

What is claimed is:

1. A puncture support device comprising processing circuitry configured to:
    acquire three-dimensional volume data;
    set a puncture target in the volume data;
    set puncturable regions on an image including a body surface of a subject and the puncture target in the volume data, the puncturable regions existing on the body surface, each of the puncturable regions on the body surface being set within a circle centered on the puncture target and whose radius is a depth at which a puncture needle used is puncturable;
    extract linear puncture routes of each of the puncturable regions, the linear puncture routes each being from each point of the puncturable regions on the body surface to the puncture target;
    calculate safety degrees of the respective linear puncture routes for each puncturable regions, based on a distance between each of the linear puncture routes and a protection target and on a coefficient of the protection target;

classify the puncturable regions into groups based on the safety degrees of the linear puncture routes for each puncturable regions;

set candidates of puncture insertion points for puncturing the puncture target on puncturable regions classified into a predetermined group of the groups; and display, on a display, a superimposed image in which an image including the classified puncturable regions, safety degrees of the respective classified puncturable regions, and the candidates on the respective puncturable regions classified into the predetermined group is superimposed on the body surface a body surface image of the subject taken from outside the subject, the body surface image not including an internal structure of the body surface of the subject.

2. The puncture support device according to claim 1, wherein the processing circuitry is configured to:

set the protection target in a region of a puncture needle reachable range;

extract, when the protection target is set in the region of the puncture needle reachable range, the puncture route from each of the puncturable regions existing on the body surface to the puncture target, based on a region of a first puncture needle reachable range in which the protection target is removed from the region of the puncture needle reachable range; and calculate the safety degree of the puncture route.

3. The puncture support device according to claim 1, wherein the processing circuitry is configured to:

set a non-puncturable region impossible to be punctured in a region of a puncture needle reachable range;

extract, when the non-puncturable region is set in the region of the puncture needle reachable range, a puncture route from each of the puncturable regions existing on the body surface to the puncture target, based on a region of a second puncture needle reachable range in which the non-puncturable region is removed from the region of the puncture needle reachable range; and calculate the safety degree of the puncture route.

4. The puncture support device according to claim 1, wherein the processing circuitry is configured to calculate the safety degree based on a positional relationship between the puncture route and the protection target, the puncture route connecting the each of the puncturable regions existing on the body surface to the puncture target.

5. The puncture support device according to claim 1, wherein the processing circuitry is configured to display a candidate region of the puncture insertion point based on at least either an area of each of the puncturable regions and a distance of the puncture route with a center of gravity of each of the puncturable regions classified into the predetermined group being the puncture insertion point.

6. The puncture support device according to claim 1, wherein the processing circuitry is configured to:

accept an input of a virtual puncture insertion point for virtual puncture in the displayed candidate region; and display, when the input of the virtual puncture insertion point is accepted, puncture support information associated with the virtual puncture insertion point on the display.

7. The puncture support device according to claim 1, further comprising a projector configured to project, on a subject, each of the puncturable regions existing on the body surface, wherein the processing circuitry is configured to use the projector to project the candidate region of the puncture insertion point on the body surface of the subject.

8. The puncture support device according to claim 1, wherein each of the classified puncturable regions is displayed in a display format according to a type of the group.

9. The puncture support device according to claim 8, wherein the type of the group corresponds to a relative safety degree.

* * * * *